United States Patent [19]
Stine et al.

[11] Patent Number: 5,456,914
[45] Date of Patent: Oct. 10, 1995

[54] **TRANSTHORACIC INTRAPULMONARY IMMUNIZATION AGAINST *ACTINOBACILLUS PLEUROPNEUMONIAE***

[75] Inventors: Douglas L. Stine; Subramaniam Srikumaran; Marvin B. Rhodes, all of Lincoln, Nebr.

[73] Assignee: Board of Regents of the University of Nebraska, Lincoln, Nebr.

[21] Appl. No.: 9,569

[22] Filed: Jan. 26, 1993

[51] Int. Cl.$^6$ .......................... A61K 39/102; A61K 39/02
[52] U.S. Cl. ..................................... 424/256.1; 424/234.1; 424/825
[58] Field of Search ................................. 424/88, 89, 92, 424/184.1, 204.7, 234.1, 256.1, 825; 435/69.3

OTHER PUBLICATIONS

A. Confer et al., "Immunologic Response to *Pasteurella haemolytica* and Resistance Against Experimental Bovine Pasteurellosis, Induced by Bacterins in Oil Adjuvants", Am. J. Vet. Res., 48:163 (1987).
Confer et al. Am J. Vet Res 48(2):163–168 1987.
Purdy et al. Am J. Vet Res 52(8):1214–1220 Aug. 1991.
Yoshizawa et al. J. Lab. Clin. Med. 100(1):61–69 Jul. 1882.
Wilke et al. Am. J. Vet Res 41(11):1773–8 Nov. 1980.
Wilke et al. Am. J. Vet Res 40(12):1690–3 Dec. 1979.
Tizard, ed. an Introduction to Vet. Immunol. 1982 see pp. 178–92 Chapter 12.
Unanue et al. ed. Textbook of Immunology 2nd edition 1982 see pp. 5–7.
W. J. C. Bogaerts et al., "Immunization of Mice Against Encephalomyocarditis Virus, Infection and Immunity", 6: 513–517 (1972).
A. Confer et al., "Effect of Prior Natural Exposure to *Pasteurella haemolytica* on Resistance to Experimental Bovine Pneumonic Pasteurellosis", Am. J. Vet. Res., 45: 2622 (1984).
A. Confer et al., "Serum Antibodies to *Pasteurella haemolytica* Lipopolysaccharide: Relationship to Experimental Bovine Pneumonic Pasteurellosis", Am. J. Vet. Res., 47: 1134 (1986).
A. Confer et al., "Serum Antibodies to Antigens Derived from a Saline Extract of *Pasteurella haemolytica*: Correlation with Resistance to Experimental Bovine Pneumonic Pasteurellosis", Vet. Immunol. Immunopath., 10:265 (1985).
A. Confer et al., "Isolation of *Pasteurella haemolytica* and Correlation with Serum Antibody Response in Clinically Normal Beef Calves", Vet Microbiol., 8:601 (1983).
P. Fedorka–Cray et al., "Efficacy of a Cell Extract from *Actinobacillus (Haemophilus) pleuropneumoniae* Serotype 1 against Disease in Swine", Infusion and Immunity, 58:358–365 (1990).
M. Gentry et al., "Neutralizing Monoclonal Antibodies to *Pasteurella haemolytica* Leukotoxin Affinity–Purify the Toxin from Crude Culture Supernatants", Microbial Pathogenesis, 10:411–417 (1991).
J. A. Kasel et al., "Influenza Antibody in Human Respiratory Secretions after Subcutaneous or Respiratory Immunization with Inactivated Virus", Nature, 218:594–595 (1968).
D. S. McVey et al., "Antibodies to *Pasteurella haemolytica* Somatic Antigens in two Models of the Bovine Respiratory Disease Complex", Am. J. Vet. Res., 50:443–447 (1989).
D. S. McVey et al., "Specificity of Bovine Serum Antibody to Capsular Carbohydrate Antigens from *Pasteurella haemolytica*", J. Clin. Microbiol., 28:1151–1158 (1990).
D. A. Mosier et al., "Serum IgG and IgM Antibody Response in Cattle to Antigens of *Pasteurella haemolytica*", Vet. Immunol. Immunopath., 22:53 (1989).
P. Newman et al., "Distribution of *Pasteurella haemolytica* and *Pasteurella multocida* in the Bovine Lung Following Vaccination and Challenge Exposure as an Indicator of Lung Resistance", Am. J. Vet. Res., 43:417 (1982).
R. J. Panciera et al., "Bovine Pneumonic Pasteurellosis: Model for *Pasteurella haemolytica*– and *Pasteurella multocida*–induced Pneumonia in Cattle", Am. J. Vet. Res., 45:2532 (1984).
R. J. Panciera et al., "Bovine Pneumonic Pasteurellosis: Effect of Vaccination with Live Pasteurella Species", Am. J. Vet. Res., 45:2538 (1984).
F. Payvandi et al., "Monoclonal Antibodies for Coagglutination of *Streptococcus suis* Type 1", Vet. Microbiol., 20:349–356 (1989).
C. Purdy, "Immune Response to Pulmonary Injection of *Pasteurella haemolytica*–impregnated Agar Beads Followed by Transthoracic Challenge Exposure in Goats", Am J. Vet. Res., 51: 1629 (1990).
T. Sakata et al., "Experimental Hypersensitivity Pneumonitis in Rabbits Induced by *Trichosporon cutaneum*: Role of Local Cellular and Humoral Immune Responses", J. Clin. Lab. Immunol., 25:191 (1988).
S. Srikumaran et al., "Quantitation of Bovine Immunoglobulins in Culture Fluids by use of Sandwich Radioimmunoassay with Monoclonal Antibodies", Am. J. Vet. Res., 52:243–246 (1991).
D. Stine et al., "*Actinobacillus pleuropneumoniae*–induced Thymic Lesions in Mice And Pigs", Respiratory Diseases, Abstract 314 (about 1991).
D. Stine et al., "*Actinobacillus pleuropneumoniae*–Induced Thymic Lesions in Mice and Pigs", Infection and Immunity, 59:2885–2891 (1991).
E. Stott et al., "Immune and Histopathological Responses in Animals Vaccinated with Recombinant Vaccinia Viruses that Express Individual Geses of Human Respiratory Syncytial Virus", J. Virol., 61:3855 (1987).

(List continued on next page.)

*Primary Examiner*—Christine M. Nucker
*Assistant Examiner*—Anthony C. Caputa
*Attorney, Agent, or Firm*—Merchant, Gould, Smith, Edell, Welter & Schmidt

[57] ABSTRACT

The invention is directed to a method for immunizing an animal for the production of high levels of IgA antibodies against a lung pathogen. The method comprises administering an antigen by transthoracic injection directly into the lung of the animal, the elicited antibodies having specific activity against the administered antigen and lung pathogen of interest. The invention provides a method of stimulating the production of IgA antibodies at mucosal surfaces of the lungs to increase IgA antibody titers in lung fluids and reduce the severity of the lung disease of interest.

6 Claims, No Drawings

OTHER PUBLICATIONS

D. Van Zaane et al., "Monoclonal Antibodies against Bovine Immunoglobulins and their Use in Isotype–Specific ELISAs for Rotavirus Antibody", *J. Immunol. Meth.*, 72:427–441 (1984).

R. Walker et al., "Study of Bovine Pulmonary Response to *Pasteurella haemolytica*: Pulmonary Macrophage Response", *Am. J. Vet. Res.*, 41–1008 (1980).

R. Walker et al., "Study of Bovine Pulmonary Response to *Pasteurella haemolytica*: Specificity of Immunoglobulins Isolated from the Bovine Lung", Am. J. Vet. Res., 41:1015 (1980).

TRANSTHORACIC INTRAPULMONARY IMMUNIZATION AGAINST *ACTINOBACILLUS PLEUROPNEUMONIAE*

BACKGROUND OF THE INVENTION

Lung diseases caused by bacterial or viral agents pose a serious problem for farmers and cattle ranchers. One example, porcine pleuropneumoniae in pigs which is caused by the bacterium *Actinobacillus pleuropneumoniae*, costs pork producers millions of dollars each year. The disease has a complex pathogenesis, and a secreted cytotoxin plays an important role in the production of acute lung lesions. Another example, bovine respiratory disease complex (shipping fever), is a severe fibrinous pneumonia that has had an economic impact on feedlot and stocker cattle. Shipping fever has a complex etiology, with the probable cause of the disease being a combination of environmental stress factors and viral and bacterial infection.

To protect animals from lung disease, it is essential to achieve a sufficiently high level of IgA antibodies in the lungs to prevent adherence of invading microorganisms to mucosal surfaces and neutralize potentially damaging virulence factors. Although attempts have been made to develop methods to deliver antigens to the lungs to stimulate antibody production, there are significant drawbacks to existing methods of immunization. Administration of vaccines by intramuscular or subcutaneous injection do not provide sufficiently high levels of IgA antibodies in lung fluids. Intratracheal or intranasal delivery of antigens by cannulation or aerosolization are labor-intensive and not practical for routine or large-scale application. In addition, the ciliated mucosa of the pulmonary tract functions in a manner that removes foreign antigens, which makes it difficult to deliver a reliable and immunologically effective amount of an antigen to the lungs by such methods.

The difficulties in administering antigens to the lungs has contributed to the present lack of efficacious vaccines for the prevention of bacterial and viral-induced infections of the lungs. Therefore, a need exists for an effective, simple method for vaccinating an animal against lung disease.

SUMMARY OF THE INVENTION

This and other objects are achieved by the present invention which is directed to a method for immunizing an animal against a lung pathogen. More particularly, the method comprises administering an antigen by transthoracic injection directly into a lung of the animal, the antigen being capable of stimulating production of antibodies specific for a lung pathogen. The present method administers an effective amount of the antigen to stimulate production of an immunologically effective post-injection antibody titer of specific IgA antibodies in lung fluids of the animal. The antibodies that are produced have specific activity against the immunizing antigen and the lung pathogen against which the animal is being immunized against.

The method is useful in treating a variety of lung diseases such as, but not limited to, swine pleuropneumoniae, enzootic pneumonia, pseudorabies (PRV), bovine respiratory disease complex, pneumonic pasteurellosis, infectious rhinotracheitis (IBR), bovine viral diarrhea (BVD) virus, bovine respiratory syncytial virus (BRSV), parainfluenza virus type 3 (PI3), equine herpes virus, strangles, canine kennel cough, canine adenovirus types 1 and 2, feline respiratory disease complex, and the like.

The antigen is administered to the animal, in an amount effective to stimulate an immune response and protect against a lethal challenge of a lung pathogen such as a bacteria, virus or fungus, in the lung of the animal. Preferably, the post-injection IgA antibody titers in the lung fluids are increased by about 4-fold or greater, preferably about 8-fold or greater, than pre-injection antibody levels, as determined by radioimmunoassay (RIA), as for example, to an IgA antibody titer of about 4 to 32 as measured in a pig. It is preferred that an immunologically effective IgA antibody titer in lung fluids is reached within about 5 to 14 days following immunization with the antigen.

Antigens that may be administered according to the method include attenuated microorganisms, inactivated microorganisms, antigenic microbial components or fragments, chemically-modified antigens, recombinant antigens or vectors carrying recombinant antigens, and synthetic peptide antigens, and other like antigens, alone or in combination, as conventionally known and used in vaccine and bacterin preparations for immunizing an animal against a lung disease.

The antigen composition is in a form for administration by transthoracic intrapulmonary injection directly into the lung of the animal. Preferably, the antigen is combined with a sterile, buffered, isotonic, pharmaceutically-acceptable and compatible aqueous carrier such as saline, or saline derivative such as citrate-buffered saline, tris-buffered saline, Ringer's Solution or tissue culture medium, and the like, preferably having a physiologic pH. An antigen composition may also include a suitable compatible adjuvant such as aluminum hydroxide, paraffin-based oils, averdine, muramyl dipeptide, and the like, to stabilize the antigen in solution, and/or an immunomodulator such as a recombinant cytokine or interleukin such as IL-1, IL-5, IL-6, TGF-beta, or gamma interferon, and the like, to enhance the IgA antibody response.

The amount of antigen included in the composition is effective to stimulate secretion of IgA antibodies against the immunizing antigen and lung pathogen against which the animal is being immunized, in the lung fluids of the animal. Preferably, the composition includes an effective amount of the antigen to stimulate IgA antibody production in lung fluids of an animal to an antibody titer of about 4-fold or greater than the animal's pre-immunization IgA antibody titer level. The antigen composition may be formulated for administration as a single injection of about 0.5 to 10 ml. The composition may also be in the form for administration in a series of biweekly or monthly injections of about 0.5 to 10 ml each, until the desired level of immunity is achieved. Preferably, the composition is formulated for biweekly administration to the animal.

The present method of immunizing an animal against lung disease provides a level of IgA antibody titers in lung fluids of the animal that is higher than that provided by conventional immunization methods that deliver antigens to the lungs systemically by intramuscular or subcutaneous injection, or directly by intratracheal or intranasal delivery, including aerosolization.

The method of the invention also stimulates production of serum IgA antibodies to levels that are the same or higher than those provided according to other known vaccination techniques. The achievement of a higher level of serum IgA antibody titers by the present method, preferably about 4 to 16-fold as compared to pre-injection IgA antibody titers, may result in the subsequent transport and secretion of IgA antibodies at mucosal sites distant from the lung, as for example, the gastrointestinal tract, mammary gland, and the like, in an effective immunizing amount to provide enhanced protection against pathogens in those organs. In addition, the present method of administering an antigen to the lung of an animal may also stimulate production of IgG antibody levels in lung fluids and blood serum that are similar to or higher than antibody levels provided according to conventional vaccination techniques. IgG antibody titers in lung fluids are preferably raised by about 4 to 32-fold as compared to conventional vaccination techniques when measured by an ELISA assay, and IgG antibody titers are preferably raised in the blood serum of the animal by about 5 to 10-fold as compared to pre-injection titers, or an about 2 to 4-fold increase over conventional vaccination techniques, when measured by ELISA assay.

Advantageously, the present method of vaccination requires no anesthetic or tranquilization procedure, and no surgical preparation other than, cleaning of the injection site on the skin of the animal. The method is simple to perform, making it particularly useful for farmers and veterinarians to immunize animals on a large scale against a lung disease or disorder. The present method enhances the use of current vaccines and bacterins that contain antigens for stimulating antibodies specific for a lung pathogen, and provides for the development of new antigen and adjuvant formulations for use in stimulating antibody levels in lung fluids of the animal.

Moreover, due to the manner of immunization and method of injection, animals immunized according to the method of the invention develop fewer granulomas and necrotic lesions in animal-derived body organs and meat such as beef, pork and lamb. In circumstances where granulomatous lesions do occur, these lesions are confined to lung tissues that are routinely discarded as non-consumable carcass byproducts. As a result, the method enhances the value of an animal and the palatability and appearance of meat products to better meet consumer-based food standards.

DETAILED DESCRIPTION OF THE INVENTION

The present invention provides a method of immunizing an animal against a lung disease caused by a bacterial, viral, or other microbial lung pathogen. Immunization using the method of the invention involves administering an effective amount of an antigen by direct injection into a lung of the animal by transthoracic intrapulmonary injection. The antigen employed is capable of stimulating the production of IgA antibodies specific for the microbial pathogen which is the causative agent of the lung disease for which the animal is being immunized. The invention provides a highly effective method of stimulating the production of IgA antibodies at mucosal surfaces of the lungs to increase IgA antibody titers in lung fluids.

The method is useful for immunizing animals against a variety of pathogens that are the causative agents of lung diseases or disorders in animals, such as cows, sheep, horses, pigs, chickens, and other livestock, and dogs, cats, and other domesticated animals. Examples of lung diseases that may be immunized against according to the invention include, but are not limited to, bacterially- and mycotically-induced diseases caused, for example, by *Actinobacillus pleuropneumoniae* (porcine pleuropneumonia), *Mycoplasma hyopneumoniae* (enzootic pneumonia), *Hemophilus parasuis, Streptococcus suis, Salmonella cholerasuis,* and the like, in swine; *Pasteurella haemolytica, P. multocida,*

*Haemophilus somnus,* and the like, in cattle; *Bordetella bronchiseptica,* and the like, in dogs; and *Cryptococcus neoformans* in cats; and the like. Examples of virus-induced diseases that may be treated according to the invention, include, but are not limited to, infections caused by components of bovine respiratory disease complex, for example, infectious rhinotracheitis virus (IBRV), bovine viral diarrhea virus (BVDV), bovine respiratory syncytial virus (BRSV) parainfluenza virus type 3 (PI3), and the like, in cattle; pseudorabies virus (PRV), influenza, swine infertility and reproductive syndrome virus (SIRS virus), and the like, in swine; feline calicivirus, feline viral rhinotracheitis virus, and the like, in cats; and distemper, parainfluenza, and adenovirus types 1 and 2, and the like, in dogs; and similar respiratory pathogens in other livestock and domestic animals.

In the present method, an antigen is administered to the animal by transthoracic injection directly into the lung. The preferred site for deposition of the antigen preparation is in the pulmonary parenchyma of the right or left caudal lung lobe. The exterior surface location of the injection site, and the length of the needle used may be modified according to the anatomy of the species and breed of animal being treated, as known in the art. For example, for weaning age swine, location of the injection site may be determined by counting seven rib spaces proceeding cranially from the last rib; for Landrace swine, eight rib spaces would be counted. For proper location of the lung lobe, a standard veterinary anatomy text would be consulted, as for example, Popekso's Atlas of Topographical Anatomy of Domestic Animals (4th ed.), Vol. 2, W. B. Saunders Co., Philadelphia, Pa. (1984), the disclosure of which is incorporated by reference herein.

An effective amount of the antigen is administered to the animal according to the method of the invention to stimulate secretion of IgA antibodies into the lung and provide an effective IgA antibody titer to protect against a lethal challenge of a lung pathogen such as a bacteria, virus, or other microbe, in the lung of the animal, and, preferably, to inhibit the lytic or lesion-producing activity of the microorganism. An effective amount of antigen is administered to the lung to induce production of IgA antibodies in lung fluids to stimulate at least a 4-fold increase in IgA antibody titers above pre-injection antibody levels, preferably about a 4 to 16-fold increase, preferably about an 8 to 16-fold increase, preferably about an 8 to 10-fold increase, as measured by radioimmunoassay (RIA), as for example, an IgA antibody titer of about 4 to 32, preferably about 8 to 32, as measured in a pig. Preferably, the increase in antibody titer is reached within about 5 to 14 days, more preferably about 5 to 7 days, post-injection of the antigen.

In a preferred embodiment, the animal is vaccinated twice, once in each caudal lung lobe, approximately two weeks apart, with about 0.5 to 10 ml of an antigen composition, more preferably about 1 to 5 ml. The antigen dose and vaccination regime may be modified to achieve stimulation of maximum IgA antibody titers in the lung fluids of the animal. It is to be understood that the antigen dosage amount can readily be adjusted to administer an effective amount of the immunizing antigen to any animal. For example, the dosage amount of an antigen administered to an animal of about 25 to 50 lbs, will be within the range of about 100 to 1000 micrograms of antigen biweekly. The dosage amount of the antigen composition to be administered will depend upon the animal, the disease for which the animal is being immunized against, the animals' medical history, the size of the animal and the like. Choice of a particular formulation of ingredients in an antigen composition and dosage amount will ultimately be according to the judgment and protocol of a medical professional such as a veterinarian. Preferably, the dosage amount of the antigen is effective to increase the titer of IgA antibodies in lung fluids, specific for the immunizing antigen, to a level of at least 4-fold or greater than the level of pre-injection IgA antibody titers, preferably within about 5 to 14 days post-injection.

The method of the invention may also be combined with other conventional vaccination methods for delivering antigens to the lungs to provide a supplemental amount of the antigen being administered. For example, the antigen may be administered nasally by aerosol spray or cannulation, by intramuscular or subcutaneous injection, or other suitable technique known and used in the art, before or after administration of the antigen to the animal by transthoracic injection into the lung.

In addition to stimulating production of IgA antibodies at mucosal surfaces of the lungs, the present method also stimulates IgG antibody titers in lung fluids to levels higher than that achieved with conventional immunization techniques. Preferably, the IgG antibody titer in the lung fluids of the animal are increased to about 2 to 32 times the pre-injection IgG antibody level of the animal, preferably about 4 to 32 times, preferably about 8 to 16 times, as measured by ELISA assay, as for example, to an IgG antibody titer of about 4 to 32, preferably about 8 to 32, as measured in a pig.

The present method may also stimulate IgA, IgM and/or IgG antibody levels in the blood serum of the animal to levels that are similar to or higher than those achieved with conventional methods. Preferably, the present method increases post-injection serum IgA antibody titers of the animal to about 4 to 16 times the level of pre-injection serum IgA antibody titers, preferably about 8 to 16 times, as measured by radioimmunoassay, as for example, to an IgA antibody titer of about 4 to 128, preferably about 8 to 128, as measured in a pig. It is also preferred that the serum IgG antibody levels of the animal are increased about 2 to 10 times the pre-injection serum IgG antibody titer level of the animal, preferably about 5 to 10 times, as measured by ELISA assay, as for example, to an IgG antibody titer of about 512 to 16,384, preferably about 1,024 to 8,192, as measured in a pig. In addition, it is preferred that the serum IgM antibody level of the animal is increased by about 4 to 10-fold over pre-injection IgM antibody levels, as measured by ELISA, as for example, to an IgM antibody titer of about 4 to 512 as seen in pigs. The increased serum IgA antibody levels and subsequent transport to other organs, and secretion of IgA antibodies in high concentrations on mucosal surfaces of organs distant from the lung, may provide increased protection against pathogens of mucosal surfaces other than the lungs, as for example, pathogens of the gastrointestinal tract, pathogens in the mammary glands that cause mastitis, and the like.

A composition useful in the present invention includes an antigen that is capable of stimulating production of IgA antibodies in lung fluids of the animal, the antibodies having specific activity for the causative agent, or pathogen, of the lung disease against which the animals being immunized. The antigen may be derived from the pathogen of the lung disease, such as, a bacteria, virus or other microorganism, or antigenic fragment thereof. Examples of antigens for use in an antigen preparation include, but are not limited to, whole bacterial cells or whole viral particles; proteins, or synthetic peptides mimicking proteins, derived from bacteria and/or virus particles by conventional protein isolation techniques and/or purification methods or by recombinant DNA techniques, with or without secreted factors such as proteases, toxins, or lytic cytotoxins; whole cells supplemented with a purified lytic antigen proteins such as proteases, toxins, or lytic cytotoxins; a cell-free extract of a bacteria that includes a single antigen such as a protein, carbohydrate, lipopolysaccharide or other antigenic substance; a secreted antigen virulence factor such as a cytotoxin, antibody binding protein, protease, or outer membrane protein; a recombinant protein, virus or bacteria; and the like. Preferably, the antigen is an inactivated or killed lung pathogen or antigenic fragment thereof.

Examples of antigens useful according to the invention include those derived from a bacterial pathogen such as, but not limited to, Actinobacillus spp. such as *A. pleuropneumoniae*, MyCoplasma spp. such as *M. hyopneumonia*, Haemophilus spp. such as *H. parasuis* and *H. somnus*, Streptococcus spp. such as *S. suis*, Salmonella spp. such as *S. cholerasuis*, Pasteurella spp. such as *P. haemolytica* and *P. multocida*, Bordetella spp. such as *B. bronchiseptica*, and the like; a viral pathogen such as, but not limited to, IBRV, BVDV, BRSV, and the like; and other microbial lung pathogens such as Cryptococcus spp., Asperqillus spp., Histoplasma spp. and antigenic fragments of the microbial pathogen. For example, an antigen composition for use in a method of preventing swine pleuropneumonia may comprise a preparation of whole cells derived from *Actinobacillus pleuropneumoniae*, and/or an antigenic fragment thereof, and an antigenic virulence factor such as a cytotoxin and/or hemolysin protein, in combination with a physiologic carrier with or without an adjuvant or immunomodulator.

The composition may include a single antigen or a mixture of antigens for immunizing the animal against a single or multiple lung diseases. The antigen composition may be formulated with conventional pharmaceutically-acceptable vehicles for administration by transthoracic intrapulmonary injection. These vehicles comprise substances that are essentially nontoxic and nontherapeutic such as saline and derivatives of saline such as citrate-buffered saline, tris-buffered saline and Ringer's Solution, dextrose solution, Hank's Solution, tissue culture medium, and the like. The antigen composition may also include minor but effective amounts of pharmaceutically-acceptable adjuvants, buffers and preservatives to maintain isotonicity, physiological pH, and stability. Adjuvants useful in the composition include, but are not limited to, for example, paraffin based oils, averdine, muramyl dipeptide, and oil-in-water-based adjuvants, and the like. Examples of suitable buffers include, but not limited to, phosphate buffers, citrate buffers, carbonate buffers, TRIS buffers, and the like. Preservatives that may be used in the present composition include, but are not limited to formalin, gluteraldehyde, and the like. It is also envisioned that the antigen may be combined with a biocompatible, and optimally synergistic, immunomodulator that cooperatively stimulates IgA antibody production, as for example, but not limited to, recombinant cytokines such as TGF-beta, interferons, activating factors, chemoattractants, interleukins such as IL-1, IL-2, IL-4, IL-5, IL-6 and the like, and other like substances.

The invention will be further described with reference to various specific and preferred embodiments and techniques. However, it should be understood that many variations and modifications may be made while remaining within the spirit and scope of the invention. The disclosures of the cited references are incorporated by reference herein.

EXAMPLE 1

Methods and Procedures

Vaccine Preparation and Vaccination

A vaccine preparation was prepared as follows. Stock cultures were prepared by inoculating a colony of *Actinobacillus pleuropneumoniae* serotype 1 into 100 ml of Brain Heart Infusion (BHI) Broth (Difco Laboratories) containing 0.5 ml of a sterile 2% solution of nicotinamide adenine dinucleotide (NAD; Sigma Chemical) in saline. This culture was incubated at 37° C. for 3 hours to allow the bacteria to reach log phase growth. One ml aliquots of the culture were mixed with equal volumes of sterile BHI broth containing 30% glycerol and frozen at −70° C. until use. Thawed stock culture (0.1 ml) was transferred to a sterile test tube containing 7 ml of BHI Broth supplemented with NAD and incubated overnight at 37° C. A 1% inoculum of this overnight culture was then transferred to a shaker flask containing 100 ml of NAD supplemented BHI Broth and incubated for 4 hours to allow log phase growth of the bacteria. Bacteria were then harvested by centrifugation at 10,000 g for 20 minutes. The bacterial pellet was then resuspended in 100 ml of RPMI medium (Gibco Laboratories) supplemented with 10% gnotobiotic porcine serum. This culture was then incubated in a shaker bath at 37° C. for 2 hours. Bacteria were again harvested by centrifugation and the bacterial pellet was resuspended in 200 ml of phosphate-buffered saline containing 1% formalin. This suspension was refrigerated overnight and then checked for sterility. This suspension was then frozen until use in the vaccine preparation. The supernatant from the RPMI culture containing the secreted cytotoxin was also harvested and filter-sterilized. This sterile supernatant was then concentrated 10× in an AMICON™ stir cell using a YM 30 cellulose acetate filter membrane (Amicon Laboratories) and frozen until use.

The pleuropneumonia vaccine and control solution were prepared on the day of vaccination. One ml of the thawed 10× RPMI supernatant was added to 0.5 ml of the thawed bacterial cell preparation. This preparation was mixed with 0.5 ml of Freund's Incomplete Adjuvant until an emulsion was formed. Animals were vaccinated with 2 ml of this preparation by: (1) intramuscular (IM) injection into the cervical neck muscle; or (2) transthoracic intrapulmonary (TTIP) injection into the lung. Control groups of animals were vaccinated by: (1) intramuscular injection in the neck; or (2) by TTIP injection into the lung with a control solution containing RPMI and 0.5 ml of Freund's incomplete adjuvant. Animals were bled before vaccination for Day 0 serum antibody analysis. Animals were revaccinated 14 days later either in the opposite cervical neck muscle or the opposite lung lobe. Animals were re-bled, and lung lavages were harvested 2 weeks following the second vaccination. Animals were challenged 10 days later with homologous virulent *Actinobacillus pleuropneumoniae* serotype 1 organisms by pressurized aerosolization. Animals were monitored over the next 48 hours for clinical signs of disease. Animals dying acutely were immediately necropsied for determination of weight gain and lung lesions. All surviving animals were necropsied 48 hours after challenge to determine % pneumonic lung lesions and % weight gain.

Transthoracic Injection of Vaccine

The vaccine or control solution was administered by transthoracic pulmonary injection into a lung lobe of the test animals as follows. Following the curvature of the caudal aspect of the seventh rib, the injection of the vaccine was made cranial to the lateral surface of the eighth rib, one-third of the ventral distance between the vertebrae and the xiphoid process of the sternum, using a 20 gauge needle, 1½ inches in length. The needle was introduced into the thorax of the animal to the hub of the needle, and the syringe aspirated prior to injection to properly seed the needle in the lung parenchyma. The injection site may also be determined by locating the xiphoid process of the sternum and moving directly dorsally two-thirds of the distance between the xiphoid process and the spine. The injection may then be made into the lung of the animal as described above.

Analysis

IgA and IgG antibody titers to bacterial whole cells were measured in lavage fluid and in serum. IgG antibody titers were measured by an enzyme-linked immunosorbent assay (ELISA) according to the method of F. Payvandi et al., *Veterinary Microbiology* 20:349–356 (1983). IgA antibody titers to bacterial cells were measured in an indirect radioimmunoassay (RIA) by modification to the method of Srikumaran et al., *AJVR* 52(2):243–246 (1991); and Van Zaane & Itzemman, *J. Immunol. Methods* 72:427–441 (1984). Cytotoxin-neutralizing antibody titers were measured in sera using a tetrazolium dye reduction assay according to the method of Gentry et al., *Microb. Path.* 10:411–417 (1991), the disclosure of which is incorporated by reference herein.

EXAMPLE 2

Comparison of Transthoracic Vaccination and Intramuscular Injection (Trial 1)

Transthoracic vaccination trial 1 was conducted to evaluate whether a transthoracic vaccination route would provide enhanced levels of protection from pneumonic disease as compared to an intramuscular route of vaccination. Pigs were divided into the following three groups: (1) a control group vaccinated with the control solution as described in Example 1; (2) an intramuscular (IM) group vaccinated with a 2-ml injection of the pleuropneumonia vaccine described in Example 1 in the cervical neck muscle on days 0 and 14; and (3) a transthoracic (TT) group vaccinated with the identical pleuropneumonia vaccine as the IM group on the same days, by transthoracic injection into the right caudal lung lobe on day 0 and the left caudal lung lobe on day 14. Pigs were challenged on day 21 with homologous virulent *A. pleuropneumoniae* serotype 1 organisms by pressurized aerosolization. Animals were held in dorsal recumbency while a nasal cannula attached to a polypropylene tube was placed in the left nares of the animal. The polypropylene tube was connected to a vacuum pump capable of generating 7–10 psi of pressure. The bacterial inoculum was introduced into the tubing via a 3-way stop-cock and the inoculum was then aerosolized. The tubing was further flushed with a 10 ml saline rinse as part of the aerosolized inoculum for each animal.

TABLE 1

| | Serum Cytotoxin Neutralization Titer | | | |
|---|---|---|---|---|
| Group | Pig # | Day 0 | Day 21 | Mean Titer |
| Control | A | 0 | 0 | 0 |
| | B | 0 | 0 | |
| IM[a] | 12 | 0 | 4 | 27 |
| Vaccin. | 13 | 0 | 32 | |
| | 14 | 0 | 8 | |
| | 15 | 0 | 64 | |
| TT[b] | 16 | 0 | 32 | 44 |

TABLE 1-continued

| | Serum Cytotoxin Neutralization Titer | | | |
|---|---|---|---|---|
| Group | Pig # | Day 0 | Day 21 | Mean Titer |
| Vaccin. | 17 | 0 | 128 | |
| | 18 | 0 | 8 | |
| | 19 | 0 | 8 | |

[a] IM = intramuscular vaccination.
[b] TT = transthoracic vaccination.

The data in Table 1 shows that the TTIP vaccination technique stimulates a neutralizing serum antibody response that is equivalent to or greater than the neutralizing response elicited by conventional vaccination techniques.

TABLE 2

| | | Clinical Evaluation at 24 hrs. Post-Challenge | | | |
|---|---|---|---|---|---|
| Group | Pig # | Dyspnea[a] | Depression[a] | Total | Group Mean |
| Control | A | 5 | 5 | 10 | (both pigs died) |
| | B | 5 | 5 | 10 | 10.0 |
| IM[b] | 12 | 2 | 2 | 4 | (pig died 48 hrs. PI[c]) |
| Vaccin. | 13 | 4 | 3 | 7 | |
| | 14 | 3 | 3 | 6 | 5.5 |
| | 15 | 2 | 3 | 5 | |
| TT[d] | 16 | 0 | 0 | 0 | 0.0 |
| Vaccin. | 17 | 0 | 0 | 0 | |
| | 18 | 0 | 0 | 0 | |
| | 19 | 0 | 0 | 0 | |

[a] Dyspnea and depression were evaluated on a scale of 0 to 4, with 0 being normal and 4 being clinically severe. A score of 5 was given to any animal that died. Dyspnea was defined as forced or labored breathing while in a standing or recumbent position. Depression was defined as lethargy, a reluctance to move and inappetence.
[b] IM = intramuscular vaccination.
[c] PI = post-injection.
[d] TT = transthoracic vaccination.

The data in Table 2 illustrates that TTIP vaccination provided significantly better protection for animals from the clinical signs of pneumonia as compared to conventional vaccination techniques.

TABLE 3

| Group | Pig # | % Pneumonic Lung Lesions[a] | Group Mean |
|---|---|---|---|
| Control | A | 46.75 | 41.25 |
| | B | 36.25 | |
| IM[b] | 12 | 12.25 | 19.25 |
| Vaccin. | 13 | 43.00 | |
| | 14 | 14.50 | |
| | 15 | 7.25 | |
| TT[c] | 16 | 5.00 (pleural adhesion) | 1.86 |
| Vaccin. | 17 | 0.00 (pleural adhesion) | |
| | 18 | 1.85 | |
| | 19 | 0.60 (granuloma) | |

[a] Pigs were necropsied at 48 hours after challenge, or immediately after acute death.
[b] IM = intramuscular vaccination.
[c] TT = transthoracic vaccination.

The data in Table 3 shows that TTIP vaccination provided a significantly higher level of protection from bacterially-induced lung lesions than conventional methods. The granuloma and fibrous pleural adhesions observed in TTIP vaccinates were typical responses to the adjuvant used in the vaccine preparation.

Results

The above results show that transthoracic vaccination provides enhanced protection from clinical disease and pneumonic lung lesions compared to vaccination by an intramuscular route using an identical vaccine. The transthoracically (TT) vaccinated group showed equivalent or higher serum cytotoxin neutralizing responses, and no difference in weight gain (data not shown) as compared to the intramuscularly (IM) vaccinated group.

EXAMPLE 3

Comparison of Transthoracic Vaccination and Intramuscular Injection (Trial 2)

Transthoracic vaccination trial 2 was conducted to determine if the transthoracic vaccination route of the invention enhanced local respiratory immune responses (i.e., increased levels of IgG and IgA antibodies in lung fluids), stimulates systemic humoral immunity (i.e., increased serum levels of IgG and IgA antibodies to bacterial cells and induced neutralizing antibodies to the bacterial cytotoxin), and provides enhanced protection from clinical disease and pneumonic lung lesions as compared to intramuscular vaccination.

Twenty-four pigs were divided into the following 3 groups: (1) control pigs receiving a control solution as described in Example 1, either by intramuscular (IM) injection into the cervical neck muscle, or by transthoracic (TT) injection into a caudal lung lobe; (2) an intramuscular (IM) group receiving an identical A. pleuropneumoniae vaccine as that described in Examples 1 and 2, by intramuscular injection into the cervical neck muscle; and (3) a transthoracic (TT) group receiving an A. pleuropneumoniae vaccine transthoracically into a caudal lung lobe, as described hereinabove in Example 2. All pigs were vaccinated on days 0 and 15. On day 32, all pigs were bled and lung lavaged with 50 ml of saline for analysis of serum and bronchoalveolar levels of IgG and IgA antibodies. On day 37, all pigs were challenged as described in Example 2 with homologous virulent A. pleuropneumoniae. Pigs were necropsied immediately after acute death or 48 hours after challenge.

TABLE 4

| | Serum Cytotoxin Neutralization Titer[a] | | | |
|---|---|---|---|---|
| Group | Pig # | Day 0 | Day 21 | Mean Titer |
| Cont. | 26 | 0 | 0 | 0.5 |
| IM[b] | 27 | 0 | 0 | |
| Cont. | 28 | 0 | 0 | |
| TT[c] | 29 | 0 | 0 | |
| | 29 | 0 | 0 | |
| | 30 | 0 | 0 | |
| | 31 | 0 | 0 | |
| | 32 | 0 | 0 | |
| | 33 | 0 | 4 | |
| IM | 34 | 0 | 32 | 44.5 |
| Vaccin. | 35 | 0 | 64 | |
| | 36 | 0 | 64 | |
| | 37 | 0 | 64 | |
| | 38 | 0 | 4 | |
| | 39 | 0 | 64 | |
| | 40 | 0 | 32 | |
| | 41 | 0 | 32 | |
| TT | 42 | 0 | 64 | 93.0 |
| Vaccin. | 43 | 0 | 16 | |
| | 44 | 0 | 512 | |
| | 45 | 0 | 64 | |
| | 46 | 0 | 32 | |
| | 47 | 0 | 16 | |
| | 48 | 0 | 8 | |
| | 49 | 0 | 32 | |

TABLE 4-continued

| Serum Cytotoxin Neutralization Titer[a] | | | | |
|---|---|---|---|---|
| Group | Pig # | Day 0 | Day 21 | Mean Titer |

[a]No cytotoxin neutralizing activity was found in lavage fluids from any group tested.
[b]IM = intramuscular vaccination.
[c]TT = transthoracic vaccination.

The data in Table 4 shows that TTIP vaccination stimulates a neutralizing serum antibody response that is equivalent or greater than the neutralizing antibody response elicited by conventional vaccination.

TABLE 5

| | | Clinical Evaluation 24 hours Post Challenge | | | |
|---|---|---|---|---|---|
| Group | Pig # | Dyspnea[a] | Depression | Total | Group Mean |
| Cont. | 26 | 4 | 3 | 7 | (died 48 hr. PI[b]) |
| IM[c] | 27 | 5 | 5 | 10 | (pig died) |
| Cont. | 28 | 3 | 3 | 6 | (died 48 hr. PI) |
| TT[d] | 29 | 3 | 3 | 6 | (died 48 hr. PI) |
| | 30 | 3 | 3 | 6 | 6.88 |
| | 31 | 3 | 4 | 7 | |
| | 32 | 3 | 2 | 5 | |
| | 33 | 4 | 4 | 8 | |
| IM | 34 | 2 | 2 | 4 | 2.75 |
| Vaccin. | 35 | 3 | 2 | 5 | |
| | 36 | 2 | 2 | 4 | |
| | 37 | 2 | 1 | 3 | |
| | 38 | 2 | 1 | 3 | |
| | 39 | 1 | 0 | 1 | |
| | 40 | 0 | 0 | 0 | |
| | 41 | 1 | 1 | 2 | |
| TT | 42 | 1 | 1 | 2 | 1.75 |
| Vaccin. | 43 | 0 | 1 | 1 | |
| | 44 | 0 | 0 | 0 | |
| | 45 | 0 | 0 | 0 | |
| | 46 | 1 | 1 | 2 | |
| | 47 | 1 | 1 | 2 | |
| | 48 | 3 | 2 | 5 | |
| | 49 | 1 | 1 | 2 | |

[a]Dyspnea and depression were evaluated on a scale from 0–4 with 0 considered normal and 4 being clinically severe. A score of 5 was given to an animal which died. Dyspnea was defined as forced or labored breathing while in a standing or recumbent position. Depression was defined as lethargy, a reluctance to move and inappetence.
[b]PI = post-injection.
[c]IM = intramuscular vaccination.
[d]TT = transthoracic vaccination.

The results in Table 5 show that TTIP vaccination provided significantly better protection in animals from the clinical signs of bacterially-induced pneumonia as compared to conventional vaccination.

TABLE 6

| Group | Pig # | % Pneumonic Lung Lesions | Group Mean |
|---|---|---|---|
| Control | 26 | 53.75 | 51.68 |
| IM[a] | 27 | 52.70 | |
| Control | 28 | 68.75 | |
| TT[b] | 29 | 68.25 | |
| | 30 | 54.25 | |
| | 31 | 41.50 | |
| | 32 | 18.75 | |
| | 33 | 55.50 | |
| IM | 34 | 13.00 | 16.09 |
| Vaccin. | 35 | 45.00 | |
| | 36 | 16.15 | |
| | 37 | 0.25 | |
| | 38 | 21.25 | |

TABLE 6-continued

| Group | Pig # | % Pneumonic Lung Lesions | Group Mean |
|---|---|---|---|
| | 39 | 13.50 | |
| | 40 | 8.25 | |
| | 41 | 11.30 | |
| TT | 42 | 5.25 | 9.10 |
| Vaccin. | 43 | 2.50 | |
| | 44 | 0.00 | |
| | 45 | 5.50 | |
| | 46 | 12.95 | |
| | 47 | 0.00 | |
| | 48 | 41.25 | |
| | 49 | 5.00 | |

[a]IM = intramuscular vaccination.
[b]TT = transthoracic vaccination.

The data in Table 6 illustrates that both conventional (IM) vaccination and TTIP vaccination provided significant protection from bacterially-induced lung lesions when compared to control animals and that TTIP vaccinates showed enhanced protection from bacterially-induced lung lesions when compared to conventional vaccinates.

TABLE 7

| Group Mean IgG Titers to APP[a] Bacterial Cells | | | | |
|---|---|---|---|---|
| | Serum Titer | | Lavage Fluid Titer[e] | |
| Group | Day 0 | Day 32 | Day 0 | Day 32 |
| Control | 8 | 88 | ND[b] | 0.00 |
| IM[c] Vaccin. | 8 | 1472 | ND | 1.75 |
| TT[d] Vaccin. | 32 | 3840 | ND | 10.29 |

[a]APP = Actinobacillus pleuropneumoniae
[b]ND = not determined
[c]IM = intramuscular vaccination
[d]TT = transthoracic vaccination
[e]Lavage fluids were collected by flushing and then quickly aspirating 50 ml of sterile saline from a main lung bronchus.

The data in Table 7 shows that TTIP vaccinates possessed significantly higher lung fluid IgG antibody levels specific for bacterial cells prior to bacterial challenge. TTIP vaccinates also possessed bacterial-specific IgG antibody levels in the blood serum that were equivalent to or higher than conventional (IM) vaccinates prior to bacterial challenge.

TABLE 8

| Group Mean IgA Titers to APP[a] Bacterial Cells | | | | |
|---|---|---|---|---|
| | Serum Titer | | Lavage Fluid Titer[e] | |
| Group | Day 0 | Day 32 | Day 0 | Day 32 |
| Control | 8 | 10.0 | ND[b] | 0.5 |
| IM[c] Vaccin. | 7 | 19.5 | ND | 0.5 |
| TT[d] Vaccin. | 8 | 53.5 | ND | 8.6 |

[a]APP = Actinobacillus pleuropneumoniae
[b]ND = not determined
[c]IM = intramuscular vaccination
[d]TT = transthoracic vaccination
[e]Lavage fluids were collected by flushing and then quickly aspirating 50 ml of sterile saline from a main lung bronchus.

The data in Table 8 illustrates that TTIP vaccinates possessed significantly higher titers of bacterial-specific IgA antibodies both in lung fluids and in blood serum as compared to conventional vaccinates.

Results

The results of Trial 2 show that transthoracic vaccination provided enhanced protection from clinical disease and lung lesions, enhanced lung lavage fluid IgG and IgA antibody levels, and enhanced blood serum IgA antibody titers as compared to intramuscular vaccination.

What is claimed is:

1. A method for vaccinating an animal against *Actinobacillus pleuropneumoniae,* comprising:

administering a composition comprising a formalin-treated *Actinobacillus pleuropneumoniae* by transthoracic injection directly into the parenchyma of a lung of an animal, the composition being administered in an amount effective to stimulate production of an immunologically-effective post-injection antibody titer of specific IgA antibodies for *Actinobacillus pleuropneumoniae* in lung fluids of the animal.

2. The method according to claim 1, wherein the composition further comprises a pharmaceutically-acceptable aqueous carrier having a physiologic pH.

3. The method according to claim 2, wherein the composition further comprises an adjuvant or immunomodulator.

4. The method according to claim 2, wherein the composition is administered as a single injection of about 0.5 to 10 ml.

5. The method according to claim 2, wherein the composition is administered in two or more injections of about 0.5 to 10 ml each.

6. The method according to claim 2, wherein the composition is administered in a series of injections of about 0.5 to 10 ml each until an about 4-fold increase in the IgA antibody titer, as compared to a level prior to the injection of the antigen, is reached.

* * * * *

UNITED STATES PATENT AND TRADEMARK OFFICE
CERTIFICATE OF CORRECTION

PATENT NO. : 5,456,914

DATED : October 10, 1995

INVENTOR(S) : Stine et al.

It is certified that error appears in the above-identified patent and that said Letters Patent is hereby corrected as shown below:

At cols. 8-9 (bridging), TABLE 1 should read as:

TABLE 1

Serum Cytotoxin Neutralization Titer

| Group | Pig # | Day 0 | Day 21 | Mean Titer |
|---|---|---|---|---|
| Control | A | 0 | 0 | |
| | B | 0 | 0 | 0 |
| IM[a] Vaccin. | 12 | 0 | 4 | |
| | 13 | 0 | 32 | |
| | 14 | 0 | 8 | |
| | 15 | 0 | 64 | 27 |
| TT[b] Vaccin. | 16 | 0 | 32 | |
| | 17 | 0 | 128 | |
| | 18 | 0 | 8 | |
| | 19 | 0 | 8 | 44 |

UNITED STATES PATENT AND TRADEMARK OFFICE
CERTIFICATE OF CORRECTION

PATENT NO. : 5,456,914

DATED : October 10, 1995

INVENTOR(S) : Stine et al.

It is certified that error appears in the above-identified patent and that said Letters Patent is hereby corrected as shown below:

At col. 9, lines 16-31, TABLE 2 should read as:

TABLE 2

Clinical Evaluation at 24 hrs. Post-Challenge

| Group | Pig # | Dyspnea[a] | Depression[a] | Total | Group Mean |
|---|---|---|---|---|---|
| Control | A | 5 | 5 | 10 | (both pigs died) |
|  | B | 5 | 5 | 10 | 10.0 |
| IM[b] Vaccin. | 12 | 2 | 2 | 4 |  |
|  | 13 | 4 | 3 | 7 | (pig died 48 hrs. PI[c]) |
|  | 14 | 3 | 3 | 6 |  |
|  | 15 | 2 | 3 | 5 | 5.5 |
| TT[d] Vaccin. | 16 | 0 | 0 | 0 |  |
|  | 17 | 0 | 0 | 0 |  |
|  | 18 | 0 | 0 | 0 |  |
|  | 19 | 0 | 0 | 0 | 0.0 |

UNITED STATES PATENT AND TRADEMARK OFFICE
CERTIFICATE OF CORRECTION

PATENT NO. : 5,456,914

DATED : October 10, 1995

INVENTOR(S) : Stine et al.

It is certified that error appears in the above-identified patent and that said Letters Patent is hereby corrected as shown below:

At col. 9, lines 43-55, TABLE 3 should read as:

TABLE 3

| Group | Pig # | % Pneumonic Lung Lesions[a] | Group Mean |
|---|---|---|---|
| Control | A | 46.75 | |
| | B | 36.25 | 41.25 |
| IM[b] Vaccin. | 12 | 12.25 | |
| | 13 | 43.00 | |
| | 14 | 14.50 | |
| | 15 | 7.25 | 19.25 |
| TT[c] Vaccin. | 16 | 5.00 (pleural adhesion) | |
| | 17 | 0.00 (pleural adhesion) | |
| | 18 | 1.85 | |
| | 19 | 0.60 (granuloma) | 1.86 |

UNITED STATES PATENT AND TRADEMARK OFFICE
CERTIFICATE OF CORRECTION

PATENT NO. : 5,456,914

DATED : October 10, 1995

INVENTOR(S) : Stine et al.

It is certified that error appears in the above-identified patent and that said Letters Patent is hereby corrected as shown below:

At col. 10, lines 41-67, TABLE 4 should read as:

TABLE 4

Serum Cytotoxin Neutralization Titer[a]

| Group | Pig # | Day 0 | Day 21 | Mean Titer |
|---|---|---|---|---|
| Cont. | 26 | 0 | 0 | |
| IM[b] | 27 | 0 | 0 | |
| | 28 | 0 | 0 | |
| | 29 | 0 | 0 | |
| Cont. | 30 | 0 | 0 | |
| TT[c] | 31 | 0 | 0 | |
| | 32 | 0 | 0 | |
| | 33 | 0 | 4 | 0.5 |
| IM | 34 | 0 | 32 | |
| Vaccin. | 35 | 0 | 64 | |
| | 36 | 0 | 64 | |
| | 37 | 0 | 64 | |
| | 38 | 0 | 4 | |
| | 39 | 0 | 64 | |
| | 40 | 0 | 32 | |
| | 41 | 0 | 32 | 44.5 |
| TT | 42 | 0 | 64 | |
| Vaccin. | 43 | 0 | 16 | |
| | 44 | 0 | 512 | |
| | 45 | 0 | 64 | |
| | 46 | 0 | 32 | |
| | 47 | 0 | 16 | |
| | 48 | 0 | 8 | |
| | 49 | 0 | 32 | 93.0 |

UNITED STATES PATENT AND TRADEMARK OFFICE
CERTIFICATE OF CORRECTION

PATENT NO. : 5,456,914

DATED : October 10, 1995

INVENTOR(S) : Stine et al.

It is certified that error appears in the above-identified patent and that said Letters Patent is hereby corrected as shown below:

At col. 11, lines 15-41, TABLE 5 shoud read as:

TABLE 5

Clinical Evaluation 24 hours Post Challenge

| Group | Pig # | Dyspnea[a] | Depression[a] | Total | Group Mean |
|---|---|---|---|---|---|
| Cont. | 26 | 4 | 3 | 7 | (died 48 hr. PI[b]) |
| IM[c] | 27 | 5 | 5 | 10 | (pig died) |
| | 28 | 3 | 3 | 6 | (died 48 hr. PI) |
| | 29 | 3 | 3 | 6 | |
| Cont. | 30 | 3 | 3 | 6 | |
| TT[d] | 31 | 3 | 4 | 7 | |
| | 32 | 3 | 2 | 5 | |
| | 33 | 4 | 4 | 8 | (died 48 hr. PI) |
| | | | | | 6.88 |
| IM Vaccin. | 34 | 2 | 2 | 4 | |
| | 35 | 3 | 2 | 5 | |
| | 36 | 2 | 2 | 4 | |
| | 37 | 2 | 1 | 3 | |
| | 38 | 2 | 1 | 3 | |
| | 39 | 1 | 0 | 1 | |
| | 40 | 0 | 0 | 0 | |
| | 41 | 1 | 1 | 2 | |
| | | | | | 2.75 |
| TT Vaccin. | 42 | 1 | 1 | 2 | |
| | 43 | 0 | 1 | 1 | |
| | 44 | 0 | 0 | 0 | |
| | 45 | 0 | 0 | 0 | |
| | 46 | 1 | 1 | 2 | |
| | 47 | 1 | 1 | 2 | |
| | 48 | 3 | 2 | 5 | |
| | 49 | 1 | 1 | 2 | |
| | | | | | 1.75 |

UNITED STATES PATENT AND TRADEMARK OFFICE
CERTIFICATE OF CORRECTION

PATENT NO. : 5,456,914  PAGE 6 of 7

DATED : October 10, 1995

INVENTOR(S) : Stine et al.

It is certified that error appears in the above-identified patent and that said Letters Patent is hereby corrected as shown below:

At cols. 11-12 (bridging), TABLE 6 should read as:

TABLE 6

| Group | Pig # | % Pneumonic Lung Lesions | Group Mean |
|---|---|---|---|
| Control | 26 | 53.75 | |
| IM[a] | 27 | 52.70 | |
|  | 28 | 68.75 | |
|  | 29 | 68.25 | |
| Control | 30 | 54.25 | |
| TT[b] | 31 | 41.50 | |
|  | 32 | 18.75 | |
|  | 33 | 55.50 | |
|  |  |  | 51.68 |
| IM Vaccin. | 34 | 13.00 | |
|  | 35 | 45.00 | |
|  | 36 | 16.15 | |
|  | 37 | 0.25 | |
|  | 38 | 21.25 | |
|  | 39 | 13.50 | |
|  | 40 | 8.25 | |
|  | 41 | 11.30 | |
|  |  |  | 16.09 |
| TT Vaccin. | 42 | 5.25 | |
|  | 43 | 2.50 | |
|  | 44 | 0.00 | |
|  | 45 | 5.50 | |
|  | 46 | 12.95 | |
|  | 47 | 0.00 | |
|  | 48 | 41.25 | |
|  | 49 | 5.00 | |
|  |  |  | 9.10 |

UNITED STATES PATENT AND TRADEMARK OFFICE
CERTIFICATE OF CORRECTION

PATENT NO. : 5,456,914

DATED : October 10, 1995

INVENTOR(S) : Stine et al.

It is certified that error appears in the above-identified patent and that said Letters Patent is hereby corrected as shown below:

| | | |
|---|---|---|
| TT | 42 | 5.25 |
| Vaccin. | 43 | 2.50 |
| | 44 | 0.00 |
| | 45 | 5.50 |
| | 46 | 12.95 |
| | 47 | 0.00 |
| | 48 | 41.25 |
| | 49 | 5.00 |
| | | 9.10 |

Signed and Sealed this

Third Day of December, 1996

Attest:

BRUCE LEHMAN

Attesting Officer     Commissioner of Patents and Trademarks